United States Patent [19]

Day et al.

[11] Patent Number: 4,892,545
[45] Date of Patent: Jan. 9, 1990

[54] VERTEBRAL LOCK

[75] Inventors: James L. Day; Richard B. Budde, both of Cincinnati, Ohio

[73] Assignee: Ohio Medical Instrument Company, Inc., Cincinnati, Ohio

[21] Appl. No.: 219,087

[22] Filed: Jul. 14, 1988

[51] Int. Cl.⁴ .............................................. A61F 2/44
[52] U.S. Cl. ...................................... 623/17; 606/61
[58] Field of Search ............... 623/18, 20, 17; 128/69, 128/92 R, 92 Y, 92 YM, 92 YT, 92 YW

[56] References Cited

U.S. PATENT DOCUMENTS

| | | |
|---|---|---|
| 3,426,364 | 2/1969 | Lumb . |
| 3,648,691 | 2/1972 | Lumb et al. . |
| 3,987,499 | 10/1976 | Scharbach et al. . |
| 4,041,939 | 8/1977 | Hall . |
| 4,401,112 | 8/1983 | Rezaian . |
| 4,459,708 | 7/1984 | Buttazzoni ............................ 623/18 |
| 4,479,491 | 10/1984 | Martin . |
| 4,553,273 | 11/1985 | Wu . |
| 4,554,914 | 11/1985 | Kapp et al. . |
| 4,563,778 | 1/1986 | Roche et al. ..................... 623/18 X |
| 4,599,086 | 7/1986 | Doty ..................................... 623/17 |
| 4,636,217 | 1/1987 | Ogilvie et al. ........................ 623/17 |

FOREIGN PATENT DOCUMENTS 0179695 4/1986 European Pat. Off. .............. 623/17
0973117 11/1982 U.S.S.R. ................................ 623/17

Primary Examiner—Richard J. Apley
Assistant Examiner—David J. Bender
Attorney, Agent, or Firm—Wood, Herron & Evans

[57] ABSTRACT

A vertebral lock mountable in a cavity surgically formed in a vertebra, to separate and stabilize the adjacent vertebrae above and below the cavity. Oppositely extending pins project upwardly and downwardly from a generally cylindrical body which is insertable in the cavity. The pins are fixed vertically by a spline which is slid between their inner ends, at a right angle, to prevent the pins from loosening.

9 Claims, 2 Drawing Sheets

VERTEBRAL LOCK

FIELD OF THE INVENTION

This invention relates to a vertebral lock for separating and stabilizing vertebrae where a portion of the spine has been removed surgically.

BACKGROUND

It is sometimes necessary, by reason of injury or disease, to remove a portion of a vertebra from the spinal column. In such situations, a gap is left between adjacent vertebrae above and below the removed portion, which must be bridged or spanned structurally so that the vertical load on the spine can be transmitted safely across the gap. One technique used to accomplish this is bone fusion, which coheres the vertebrae as a monolithic element. A drawback of bone fusion, however, is that it requires a long period of recovery and rehabilitation. It is also known to use spinal stabilizing devices to separate the vertebra adjacent a damaged and/or partially removed vertebra. Some such devices, as shown, e.g., in U.S. Pat. Nos. 4,553,273 and 4,401,112, may be adjusted after insertion by means of a threaded shaft to provide a precise desired spacing. A drawback of spinal stabilizers has been the difficulty of placing and fixing them in the desired position, and the possibility that they might loosen or shift after they have been implanted in the body, by reasoning of turning of the threaded shaft.

SUMMARY OF THE INVENTION

The device of the present invention overcomes the shortcomings of the known devices and methods of spinal stabilization in that it is easily implantable and positionable and, once in place, is very much less susceptible to loosening.

Structurally, the vertebral lock of this invention includes a rigid, one piece load bearing body which is shaped to be insertable in the cavity formed when part of a vertebra has been removed from the spinal column. The body has a central slot which may extend through it in the direction perpendicular to the axis of the spine, i.e., the slot is horizontal when the lock is in use. Two pin guide holes or bores extend from opposite sides of the slot, parallel to the spine axis, i.e., vertically, through the upper and lower ends of the body. Retaining pins fit slidably within the respective guide holes and project out from each end of the body. The upper and lower ends of the body fit snugly between the vertebrae above and below the cavity to receive and carry the axial load on the spine. The pins are engageable with the adjacent vertebra directly above and below the body when so engaged to secure the body in place with respect to those vertebrae. Each retaining pin has a pointed tip at its outer end beyond the end of the body for engaging the adjacent vertebra, and also has means extending across its inner end for engaging a locking means that extends into the slot and locks the pins against vertical (axial) movement. The locking means is preferably in the form of a spline or bar that is insertable into the slot in the body of the device, to hold separate, engage and secure the inner ends of the pins and thereby hold the pins against both axial (vertical) and rotational movement.

In use, after the body has been inserted into the cavity in a vertebra and the retaining pins have been inserted in the guide holes and are in engagement with the adjacent vertebrae, the locking means is inserted into the slot wherein it engages the inner ends of the retaining pins, pushes the pins apart (outwardly) in the holes, and thereby locks the pins to the body and the body to the vertebrae. With the pins thus secured by the locking spline (which is transverse to them), there is no tendency for the pins to "back out" over time or to become unscrewed. The pins are oriented vertically, in line with the axis of the spine, and are loaded by the spine in compression against the locking spline. Because the spline is perpendicular to the pins, the locking spline is not cammed out of its engagement with them.

In a preferred form, the body has flanges that project from each end of the body (i.e., the upper and lower ends of the body) parallel to the guide holes but offset outwardly from them so as to overlap the inside faces of the adjacent vertebrae. Each flange has an aperture therein to permit additional securing of the device in place, as by screwing it to the adjacent vertebrae.

BRIEF DESCRIPTION OF THE DRAWINGS

The vertebral locking device of the present invention will be further understood with reference to the accompanying drawings in which.

DETAILED DESCRIPTION OF THE DRAWINGS

Figure 1:
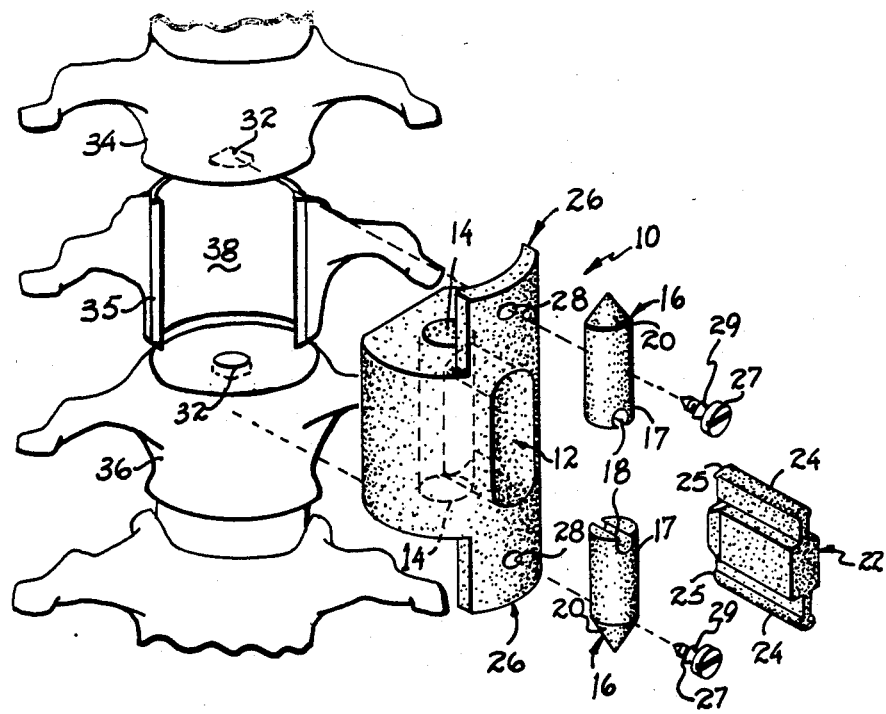
FIG. 1 is an exploded perspective view of a preferred embodiment of the invention, illustrating the device in juxtaposition to a cavity between adjacent vertebrae.
Figure 2:
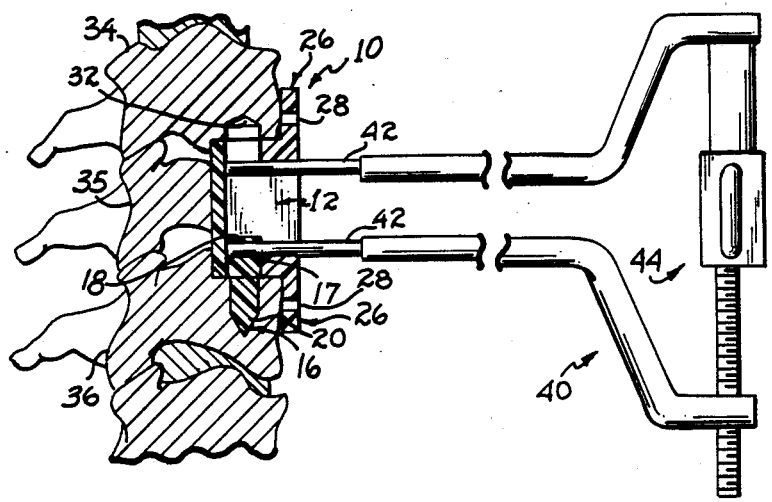
FIG. 2 is a vertical section, partially broken away, of a portion of a spinal column in which a vertebral lock of the type shown in FIG. 1 is being positioned, and also shows an instrument for inserting the retaining pins into the body of the device.
Figure 3:
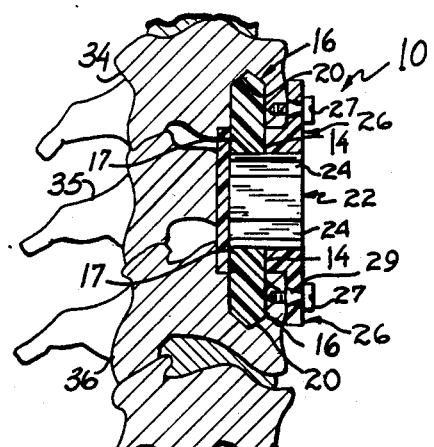
FIG. 3 is a vertical section similar to FIG. 2 but shows the vertebral lock secured in the spinal cavity.
Figure 4:
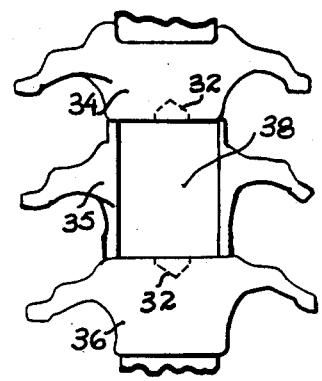
FIG. 4 is a diagrammatic front elevation of a section of the spinal column with a portion of a vertebra removed to form the cavity for the lock, and adjacent vertebrae pre-drilled to receive the retaining pins.

A preferred embodiment of the present invention is illustrated in FIGS. 1-3. The device, which is preferably made of molded plastic, has a body 10 which is preferably cylindrical with an elongated transverse central slot 12. Two opposed pin receiving guide holes 14, 14 extend perpendicularly to slot 12 through opposite ends of body 10. The holes may be and preferably are colinear. Two vertebra-engaging retaining pins 16, 16 fit slidingly within and are axially guided by the guide holes 14, 14. Each retaining pin 16 has a pointed end 20 which, when the pin is positioned in its guide hole 14, extends out from the upper or lower end of body 10, and is engageable with an adjacent vertebra as shown in FIGS. 2 and 3. Each retaining pin 16 is abutted and supported at its inner end 17, within slot 12, by slidable locking means designated generally by 22 which extends perpendicularly to each pin 16 and prevent it from being pushed axially into the body by the vertebra with which it is engaged. Locking means 22 is preferably in the form of a spline or flat bar, see FIG. 1. The inner end 17 of pin 16 preferably has a channel or socket 18 extending transversely to it. Locking means 22 has parallel ribs 24, 24 along its opposite upper and lower edges as seen in FIG. 1, and is sized to fit in slot 12 without play in the vertical direction. The ribs 24, 24 have angulated ramps 25 first at their inner ends to engage and cam outwardly the pins as they engage the respective channels 18, 18. Alternatively, the positions can be reversed: a rib can be formed on the inner end of each retaining pin to engage a channel in the respective edge of the locking bar.

For installation, each retaining pin 16 can be positioned within its guide hole 14 by insertion through slot 12, using a pin holder tool designated by 40 in FIG. 2. The pin holder has two parallel legs with tips which can be engaged in the channels 18, 18 of the pins. The legs can be moved and held apart by a threaded sleeve adjuster 44 so as to hold the pins axially apart against the vertebrae until the locking means is inserted. More specifically, tip 42 of device 40 engages channel 18 of retaining pin 16 and pin 16 is inserted into slot 12. The legs of device 40 are then spread using the adjuster 44 to push pin 16 into guide hole 14 so that pointed end 20 engages the adjacent vertebra in a pre-drilled or starter hole 32. (The hole 32 need only pierce the outer surface of the vertebra; the cancellous central bone, being softer, does not require drilling.) When the retaining pins 16, 16 are positioned in guide holes 14, 14, tool 40 is removed and locking means 22 is inserted in slot 12 to engage bar ribs 24 in channels 18 in retaining pins 16, thereby to lock the pins in place. Because locking means 22 extends into and engages pins 16, 16 perpendicularly to their axis, any compression or vertical thrust exerted by the spine on the pins acts as a compressive load on the locking means and there is no tendency for it to loosen or be cammed out of slot 12. (The ramps 25 at the leading or first end of the ribs do not extend along the length of the ribs; the ribs are parallel, excepting the ramps.)

As a means for providing additional spinal stabilization, body 10 has flanges 26, 26 which project from each end of the body parallel to guide holes 14, 14. Each flange 26 has an aperture 28 which allows the device to be secured in place for example by a screw 27, to the adjacent vertebrae as shown in FIG. 3. The screw 27 preferably has an inwardly flaring lip or shoulder 29 which, when the screw is tightened, engages the inner side of flange 26 and thereby prevents the screw from loosening.

The drawings show a portion of a human spinal column including vertebrae 34, 35 and 36. The middle vertebra 35 is depicted as having had a generally vertical cavity 38 on the front side, formed by surgical removal of a part of that vertebra. Pin locator holes 32, 32 are drilled diagonally upward and downward in vertebrae 34 and 36, above and below cavity 38, and body 10 is inserted into cavity 38. Retaining pins 16, 16 are positioned within guide holes 14, 14, which may be done as described above, to engage the starter holes in vertebrae 34 and 36. When in place, retaining pins 16, 16 project out from body 10 and into holes 32, 32 as shown in FIG. 3. At this point, the locking means 22 is inserted to push the pins into the cancellous bone and lock the device in place, and the device may be further secured with the screws 27, 27.

It will be appreciated by those skilled in the art that the vertebral lock of this invention may be made in varying sizes and body configurations for use in different vertebrae and in children as well as adults. In particular it is preferred that the distance between the upper and lower faces of body 10 correspond to the distance between vertebrae 34 and 36, so that these vertebrae will rest upon the end faces to transmit the spinal load directly through body 10.

Other variations and modifications in the structure of the device will be apparent to those skilled in the art, within the scope of the claims which follow:

What is claimed is:

1. A vertebral lock comprising:
   (a) a body seatable within a cavity formed by removal of a portion of a vertebra from a spinal column,
   (b) a central slot presented by said body,
   (c) a pair of guide holes in said body, said guide holes extending substantially perpendicularly from said slot in opposite directions through respective ends of said body,
   (d) a retaining pin axially slidably received in and axially guided by each said guide hole, each pin having a pointed tip at an outer end thereof, said tip in use projecting outwardly of said body for engaging a vertebra, each pin having an inner end which extends into said slot; and
   (e) locking member insertable into said slot perpendicularly to said pins after said pins have been projected outwardly of said body to positively abut and stop the inner ends of said pins and thereby lock the pins in said guide holes with their tips projecting outwardly of said body.

2. The vertebral lock of claim 1 wherein said locking member is a bar having opposite sides thereof which are parallel to one another, each such side having a rib extending along it, each retaining pin having a transverse channel across its inner end, said ribs interfitting into said transverse channels of said retaining pins and locking said pins to said body.

3. The vertebral lock of claim 2 wherein the transverse channels of said pins grip said ribs to resist axial movement of the pins along and away from the ribs.

4. The vertebral lock of claim 3 wherein each retaining pin has a cylindrical portion which is sized to slide in said guide hole, and the transverse channels of said retaining pins extend across said cylindrical segments.

5. The vertebral lock of claim 1 further including integral secondary attaching means for securing said body to at least one vertebra, adjacent said cavity, said attaching mean being flanges which project from said body, parallel to said guide holes.

6. The vertebral lock of claim 5 wherein said flanges have screw apertures for securing said body to adjacent vertebrae.

7. A vertebral lock comprising:
   (a) a body seatable within a cavity formed by removal of a portion of a vertebra from a signal column,
   (b) a central slot presented by said body,
   (c) a pair of guide holes in said body, said guide holes extending substantially perpendicularly from said slot in opposite directions through respective ends of said body,
   (d) a retaining pin slidably received in and axially guided by each said guide hole, each pin having a pointed tip at an outer end thereof, said tip in use projecting outwardly of said body for engaging a vertebra, each pin having an inner end which extends into said slot; and
   (e) locking means insertable into said slot perpendicularly to said pins and engaging the inner ends of said pins to lock the pins in said guide holes with their tips projecting outwardly of said body,
   wherein said central slot is elongated in the direction of said guide holes and said locking means is a bar having a width corresponding to the width of said slot.

8. The vertebral lock of claim 1 wherein each of said retaining pins has a cylindrical segment adjacent its inner end and its tip is formed by a conical segment, said cylindrical segment having a diameter substantially the same as the diameter of said guide hole such that said retaining pins slide axially within said holes, said conical portions protruding from said body when said retaining pins are locked within said holes by said locking member.

9. A vertebra lock comprising:
(a) a body seatable within a cavity formed by removal of a portion of a vertebra from a spinal column,
(b) a central slot presented by said body,
(c) a pair of guide holes in said body, said guide holes extending substantially perpendicularly from said slot in opposite direction through respective ends of said body,
(d) a retaining pin axially slidably receivable in and axially guided by each said guide hole, each pin having a cylindrical segment adjacent an inner end of the pin, said cylindrical segment extending into said slot, and a conical segment adjacent an outer end of the pin, said conical segment forming a pointed tip, said tip projecting outwardly of said body for engaging a vertebra;
(e) a locking bar having ribs along opposite sides thereof, said bar being insertable into said slot perpendicularly to said pins for locking said pins in said guide holes, said bar being non-rotatable in said slot, each of said pins having transverse channel across its inner end, said ribs interfitting said transverse channels of said pins to positively abut the inner ends of said pins and lock the pins against further axial movement; and
(f) flanges with apertures therein projecting from said body parallel to said guide holes for securing said body to adjacent vertebrae.

* * * * *